(12) United States Patent
Cockrem

(10) Patent No.: US 6,664,413 B1
(45) Date of Patent: Dec. 16, 2003

(54) PROCESS FOR PRODUCTION OF ESTERS

(75) Inventor: Michael Charles Milner Cockrem, Madison, WI (US)

(73) Assignee: A. E. Staley Manufacturing Co., Decatur, IL (US)

( * ) Notice: Subject to any disclaimer, the term of this patent is extended or adjusted under 35 U.S.C. 154(b) by 558 days.

(21) Appl. No.: 09/196,266

(22) Filed: Nov. 19, 1998

(51) Int. Cl.[7] .......................... C07C 67/36; C07C 69/52; C07C 69/02; C07C 69/66; C07C 67/08
(52) U.S. Cl. .......................... 560/204; 560/231; 560/98; 560/205; 560/179
(58) Field of Search ............................... 560/231, 204, 560/98, 205, 179

(56) References Cited

U.S. PATENT DOCUMENTS

| | | | |
|---|---|---|---|
| 1,668,806 A | 5/1928 | Gabriel | |
| 2,029,694 A | 2/1936 | Bannister | 260/535 |
| 2,334,524 A | 11/1943 | Wenker | 260/484 |
| 2,465,772 A | 3/1949 | Weisberg | 260/484 |
| 2,565,487 A | 6/1951 | Filachione | 260/484 |
| 2,722,541 A | 11/1955 | Schulz | 260/484 |
| 4,100,189 A | 7/1978 | Mercier | 260/541 |
| 4,250,328 A | * 2/1981 | Fujita et al. | 560/205 |
| 4,452,969 A | * 6/1984 | McCready | 528/279 |
| 4,780,527 A | * 10/1988 | Tong et al. | 528/279 |
| 4,868,329 A | * 9/1989 | Powanda et al. | 560/205 |
| 5,071,754 A | 12/1991 | Walkup | 435/135 |
| 5,210,296 A | 5/1993 | Cockrem | 562/589 |
| 5,252,473 A | 10/1993 | Walkup | 435/135 |
| 5,426,219 A | 6/1995 | Lehnhardt | 562/580 |
| 5,453,365 A | 9/1995 | Sterzel | 435/135 |
| 5,502,240 A | * 3/1996 | Pugach et al. | 560/99 |
| 5,723,639 A | 3/1998 | Datta et al. | 554/154 |
| 5,766,439 A | 6/1998 | Eyal et al. | 204/524 |

FOREIGN PATENT DOCUMENTS

| | | |
|---|---|---|
| DE | 206 373 | 1/1984 |
| EP | 0 812 818 A1 | 12/1997 |
| EP | 0812818 A | * 12/1997 |

OTHER PUBLICATIONS

Filachione et al., "Lactic Esters by Reaction of Ammonium Lactate with Alcohols," Industrial and Engineering Chemistry, pp. 2189–2191 (Sep. 1952).
Costello et al., "Preparation of Properties of Pure Ammonium DL–Lactate," Journal of the American Chemical Society, vol. 75, pp. 1242–1244 (1953).
"Fatty Acid Amides," Kirk–Othmer Encyclopedia of Chem. Tech., 4th Ed., vol. 2, pp. 346–356 (1992).
Coleman et al., "Acetamide," Organic Synthesis, vol. 1, p. 3–5.
House, Jr., "Decomposition of Ammonium Carbonate and Ammonium Bicarbonate and Proton Affinities of the Anions," Inorg. Nucl. Chem. Letters, vol. 16, pp. 185–187 (1980).
House, Jr., et al., "TG Studies on the Decomposition of Some Ammonium Compounds," Thermochimica Acta, vol. 42, pp. 377–381 (1980).
Filachione et al, "Purification of Lactic Acid," Industrial and Engineering Chemistry, vol. 38, pp. 228–232 (Feb. 1946).

* cited by examiner

*Primary Examiner*—Alan L. Rotman
*Assistant Examiner*—Taylor V Oh
(74) *Attorney, Agent, or Firm*—Williams, Morgan & Amerson, P.C.

(57) ABSTRACT

A process for producing an ester comprises the steps of: (a) feeding to a first vessel a feed that comprises organic acid, alcohol, and water, whereby organic acid and alcohol react to form monomeric ester and water, and whereby a first liquid effluent is produced that comprises as its components at least some ester, alcohol, and water, the components of the first liquid effluent being substantially in reaction equilibrium; and (b) feeding the first liquid effluent to a second vessel, whereby a vapor product stream and a second liquid effluent stream are produced, the vapor stream comprising ester, alcohol, and water, wherein the second vessel is maintained substantially at vapor-liquid equilibrium but not substantially at reaction equilibrium.

33 Claims, 1 Drawing Sheet

PROCESS FOR PRODUCTION OF ESTERS

BACKGROUND OF THE INVENTION

The present invention relates to processes for producing esters from the reaction of an organic acid and an alcohol.

Esters are organic chemicals of significant industrial importance, for example for use as solvents and as reagents. One way to form esters is by reacting an organic acid with an alcohol to form an ester and water, as shown in reaction (1)

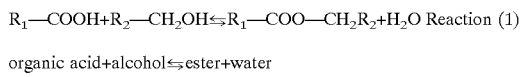

organic acid+alcohol⇌ester+water

Many esterification processes or systems focus on removal of water to drive the yield or conversion. Removal of water biases the equilibrium towards the products shown on the right hand side of Equation (1). This approach to esterification has been applied to a wide range of organic acids and alcohols.

For example, long chain alcohols that form heterogencous azeotropes with water can be used for water removal in the reaction's overhead vapors. Water removal can be easily carried out by using a higher alcohol that is sufficiently high boiling and slightly soluble in water. In addition, excess alcohol can be used to drive reaction.

Alternatively, an added azeotroping agent may be used to remove water in the case of esterification using lower alcohols such as ethanol and methanol. One example of a suitable azeotroping agent is benzene.

However, this approach to water removal to drive the reaction has met with less success with systems wherein one or both of the reagent components tend to form dimers, oligomers, polymers or side reaction products when they are dehydrated. Esterification of lactic acid is one such example. In these cases, progress has been restricted by the problem that while water removal is necessary to drive the equilibrium of reaction (1), this water removal at the same time also produces unwanted dehydration side reactions such as formation of various dimers and oligomers or lactic acid. These lead to yield loss.

The problem of oligomer formation has in the past been partially overcome by addition of significant excess alcohol, which tends to suppress the reactions that lead to formation of dimers and oligomers. However, this approach has not been entirely successful and also it has lead to higher costs for recovery of the product due to high levels of excess alcohol that must be removed.

Another approach that has been used is a single reactor wherein a batch of lactic acid or other acid is dehydrated, or is present initially at high concentration and is heated such that when the alcohol is introduced into the vessel, then ester, excess alcohol, and water formed in the reaction are flashed out of the reaction vessel.

One example of the esterification of lactic acid is given by Gabriel et al (U.S. Pat. No. 1,668,806) who prepared 1-butyl lactate by dehydrating 70% lactic acid with excess 1-butanol at 117° C., followed by addition of HCl catalyst, followed by refluxing and esterification with addition of excess 1-butanol and drawing a 1-butanol water azeotrope overhead. The process involved dehydration of the system and removal of water prior to the esterification step.

Bannister (U.S. Pat. No. 2,029,694) describes a method for producing esters that have boiling points of at least 120° C. The lactic acid and acidic catalyst are charged to a reactor and heated to the boiling point of the ester or not less than 20° C. below this temperature. The alcohol is introduced into the reactor below the surface of the hot partially dehydrated acid. The ester, water of reaction, and excess alcohol are taken off overhead. For example, methyl lactate is formed at temperatures from 130 to 140° C. by introducing methanol into partially dehydrated lactic acid. The overhead distillate is 8–10% water, 42–42% methanol, and 50% methyl lactate, by weight. For every 4.8 moles of methyl lactate produced in the system a total of 17.9 moles of methanol is fed to the system. Most or all of the water taken overhead (5.0 moles) is produced by the esterification reaction. The effective feed water level is 0.2 moles. This means that the feed streams are essentially water free.

Weisberg, Stimpson, and Miller (U.S. Pat. No. 2,465,772) mix substantially water-free lactic acid with 3 to 20 parts by weight of aliphatic alcohol of 1 to 3 carbon atoms, reacting the mixture below the boiling point and then flashing the mixture at a higher temperature. For example, for the case of formation of methyl-lactate, the mole ratio of methanol to lactic acid is at a minimum 8.5:1. It may be as high as 56 moles of methanol per mole of lactic acid.

Filachione and Fisher (Industrial Engineering and Chemistry, Volume 38, page 228, 1946) present another example of such technology. Their scheme involves bubbling excess hot alcohol, such as methanol vapor, through a hot partially dehydrated lactic acid solution at a temperature above the alcohol boiling point, whereby the lactate ester produced is removed with the alcohol vapors and any water produced from the reaction. Approximately 9 moles of methanol are required per mole of lactic acid from an 82% solution. Dramatically larger quantities of methanol are required for more dilute lactic acid feed solutions.

These methods described above typically require both excess alcohol and also dehydrated lactic acid. They are not energy efficient and also they require equipment that is large and expensive. In the cases where dehydrated lactic acid is used, the reaction temperature is typically close to that of the boiling point of the ester. In each case the reaction is conducted at the same temperature as the boiling or mass transfer.

An alternate approach is to attempt the reaction without first dehydrating the lactic acid. The following two references illustrate previous attempts that have been made to effectively utilize such an approach.

Wenker (U.S. Pat. No. 2,334,524) describes a process wherein both an esterification reactor and an adjacent hydrolysis reactor feed vapor to a common distillation column. Alcohol is removed from the top of this column and returned to the esterification reactor. The liquid product from the bottom of the column comprising largely water and ester are fed to the hydrolysis reactor. The ester is continuously hydrolyzed in that reactor to form free acid. The organic acid is 70 to 85% concentration and about 1.5 moles of alcohol are used per mole of organic acid. Reaction times are 12 to 16 hours for this system. The fractionating column is located immediately on top of the two reactors. This process appears to use a relatively low level of alcohol, but this is really the initial charge to the unsteady state system. The system is only suitable for batch esterification. At the end of the batch, the ratio of methanol to lactic acid in the esterification reactor will be very high, as much as 20:1 or more. This is because during the batch the acid is gradually removed from the esterification reactor while the alcohol is continuously returned during the run. The process will be quite energy intensive as towards the middle and end of the batch there will be a need to take large amounts of methanol or alcohol into the overheads. This process is thus not suitable for large scale, continuous efficient operation. The effective average ratio of methanol to lactic acid would be near to 10:1 if this process were to be run in multiple vessels in a configuration such as might allow continuous operation. The effective vast excess of methanol is needed to obtain high yield in this equipment and process configuration.

Franke, Gabsch, and Thieme, (East German Patent 206 373, Jan. 25, 1984) describe a similar process for formation of lactic acid esters of C1, C2 and C3 alcohols with the reaction and evaporation both occurring at reduced pressure and temperature in a modified vacuum-recirculation-evaporator. They use vacuum to operate the equipment at temperatures below the boiling point of the alcohol and use high levels of sulfuric acid as the catalyst. For example, in their example 2, they charge 2.0 liter of concentrated sulfuric acid into 15 liter of 80% crude lactic acid at 50 Torr pressure. This is over 15% W/W sulfuric acid in the initial lactic acid charge. The system is heated at 60° C. under vacuum, and then 15 to 20 liters of methanol is added slowly and continuously subsurface. As soon as the methanol contacts the lactic acid, it both reacts with the lactic acid and tends to vaporize and to carry the hot acid-alcohol-ester mixture up into the heating tube portion of the reactor and to the flash part of the reactor. The system is mixed and operates such that all three portions of the reactor—the heating, the evaporation, and the feed zone—are at essentially the same pressure, and such that the temperatures in each area are similar or perhaps the temperature in the flash area is greater than that in the reservoir due to the heat input. The liquid in the reservoir is drawn upward by convection through the heat exchanger into the vapor chamber. The liquid runs by gravity back into the reservoir. The chamber produces liquid which drains back into the reservoir and vapor. The resultant overhead condensate is 50% by weight methyl lactate. As the liquid runs back by gravity, thus the evaporation chamber and the reservoir must be at similar pressures. If the evaporation chamber was at a reduced pressure, then the liquid would not run back to the reservoir. Hence the system operates essentially identically to a single heated reactor. Other such systems can be envisaged, for example the heat could be applied in an external recirculation loop, or with internal coils, or with a jacket. In each case the vapor would be drawn off overhead as is shown in this patent.

This invention is limited to C1–C3 alcohols, low pressures, and low reaction temperatures. These low reaction temperatures require the mentioned very high levels of sulfuric acid to keep reactor volume to an economic size. However high levels of sulfuric acid, even at low temperatures, might lead to dehydration side reaction products such as dialkyl-ethers derived from the alcohols, and also various products from the degradation of lactic acid in the presence of sulfuric acid. The relative extent of these side reactions at these low temperatures is not known, but they will be minor as the yield reported in the patent is 96–98% for an extended run.

For the example of ethyl lactate, the system temperature would not exceed 78° C. This system is quite similar to earlier references wherein the alcohol mixture is introduced subsurface into the lactic acid mixture and a mixture of water, ester and alcohol removed in the overhead vapor. In their claim 2 they note that system pressures of 15 to 50 mm Hg and temperatures of 40 to 65° C. are favored. Their claims 3, 4, and 5 present how a modified vacuum-recirculation-evaporator may be used to advantage for operation of their process in a semi-continuous (i.e. semi-batch) mode. This involves charging the system with a batch of lactic acid, then operating the system with a continuous feed of alcohol. After a certain amount of run time, the lactic acid is depleted from the reactor device and a new batch is charged. This equipment involves a thermosiphon heat exchanger (2) that draws the liquid from the reactor into a vapor-liquid disengagement chamber (3) from which the liquid drains back into the reactor (1). A valve (9) regulates the flow through the heat exchanger. No mention is made of the need to balance temperature, pressure, concentration, holdup time, and catalyst concentration nor of the need for sufficient water to ensure successful operation.

The mole ratio of methanol to lactic acid in this process can be calculated from a typical example. A feed of 15 to 20 liter of methanol is contacted with 80% w/w lactic acid. Allowing for densities of these feeds, this represents a molar ratio of alcohol to acid of from 3.3:1.0 to 2.5:1.0. The feed mole ratio of water to lactic acid is about 1.24:1.

It is important to note that the methanol feed for the Franke process is not into the reactor but rather into the inside of the riser tube that feeds the evaporator/heat exchanger. The methanol will contact the hot lactic acid and tend to flash, carrying the hot mixture of methanol and lactic acid vapor and liquid, together with water and methyl lactate upwards through the heat exchanger to the flash chamber. Thus the reaction with the methanol occurs mainly as the methanol is added to vaporize and carry the hot boiling mixture up the reaction pipe through the heat exchanger to the flash area. Residence time and temperature in the flash unit and the reactor unit will be similar. The key difference between the Franke process and those of Filachione and Wenker is this equipment and mode of introducing the methanol such that the liquid and boiling vapors are carried upwards into the heat exchanger.

Their apparatus does not allow operation at temperatures above the normal boiling point of the alcohol, does not have any way to separate catalyst, and uses an unusually high level of catalyst—15% w/w sulfuric acid. The overhead vapor is 50% w/w lactic acid basis in the form of methyl lactate. This is a high level of methyl lactate in the overhead vapor. The process is however limited in the scope of operation.

Datta and Tsai (U.S. Pat. No. 5,723,639) present a more modern approach that uses pervaporation or vapor permeation to achieve dehydration. A three stage system is used comprising a reactor, a water permeation system and an ester permeation system. A pervaporation membrane is used to permeate water formed in the reactor. The water is permeated into a reduced pressure vapor space. A second membrane separation system is used to selectively remove the ester formed in the reaction. As in earlier technologies, the reaction is driven by a dehydration step.

The question that is not addressed effectively in the above patents is how to drive the reaction to high levels of conversion while (1) minimizing production of undesired side products such as dimers, oligomers, and polymers, (2) minimizing energy usage, and (3) allowing continuous operation effectively with low capital cost equipment. There is a long-standing need for improved processes for producing esters of organic acids.

SUMMARY OF THE INVENTION

The current invention concerns separation of time scales. The discovery shows that under selected conditions, reaction is minimized in the equipment where mass transfer occurs, and thus formation of unwanted side reaction products such as dimers and oligomers is avoided.

One aspect of the present invention is a process for producing an ester, comprising the steps of: (a) feeding to a first vessel a feed that comprises organic acid, alcohol, and water, whereby organic acid and alcohol react to form monomeric ester and water, and whereby a first liquid effluent is produced that comprises as its components at least some ester, alcohol, and water, the components of the first liquid effluent being substantially in reaction equilibrium; and (b) feeding the first liquid effluent to a second vessel, whereby a vapor product stream and a second liquid effluent stream are produced, the vapor stream comprising ester, alcohol, and water, wherein the second vessel is maintained substantially at vapor-liquid equilibrium but not substantially at reaction equilibrium.

In one embodiment of the invention, the first vessel is operated at a pressure $P_1$ and the second vessel is operated at a pressure $P_2$, where $P_1$ and $P_2$ are substantially the same, and the average residence time of the feed in the first vessel is at least 10 times longer than the average residence time of the first liquid effluent in the second vessel.

In another embodiment, the first vessel is operated at a temperature $T_1$ and the second vessel is operated at a second temperature $T_2$ that is sufficiently lower than $T_1$ so that the contents of the second vessel are not substantially close to reaction equilibrium.

In yet another embodiment, the first vessel is operated at a pressure $P_1$ that is from about 30–500 psig and the second vessel is operated at a pressure $P_2$ that is from about 1–14 psia.

In still another embodiment, catalyst is added to the first vessel in an amount sufficient to catalyze the formation of the ester, and where at least some of the catalyst is removed from the first liquid effluent before it enters the second vessel, so that the contents of the second vessel are not substantially close to reaction equilibrium. In certain more specific versions of this embodiment of the process, the catalyst is heterogeneous in the first vessel and is substantially not present in the second vessel. Alternatively, the catalyst is homogeneous in the first vessel and is substantially removed prior to the second vessel via washing.

Features of various embodiments of the process which can achieve the necessary separation of time scales can include:

both the temperature and pressure in the first vessel are greater than that in the second vessel;

the second vessel is operated under pressure greater than atmospheric but with short residence time (e.g., about 1 to 10 minutes);

the first vessel is operated at a liquid temperature of from 150 to 220° C. and the second vessel is operated with an exit vapor temperature of from 30 to 100° C.;

the first vessel is operated under pressure greater than atmospheric pressure; or the first vessel is operated substantially in a liquid phase with pressures sufficient to substantially suppress vaporization and with temperatures up to 220° C. without any added catalyst. In these latter systems, the organic acid (e.g., lactic acid) itself acts as the catalyst for the reaction.

In one preferred embodiment the organic acid is selected from the group consisting of mono-, di-, and tricarboxylic acids having 3–8 carbon atoms.

In another preferred embodiment the organic acid is selected from the group consisting of acetic acid, succinic acid, citric acid, malic acid, lactic acid, hydroxyacetic acid, pyruvic acid, itaconic acid, formic acid, oxalic acid, propionic acid, beta-hydroxybutyric acid, and mixtures thereof.

The alcohol preferably is an aliphatic alcohol having from 1–20 carbon atoms, most preferably an aliphatic alcohol having from 1–12 carbon atoms. Alcohols that are presently especially preferred include i-butanol, t-butanol, n-butanol, i-propanol, n-propanol, ethanol, and methanol.

The feed for the first vessel can be created by feeding a single mixed stream to the vessel. Alternatively, a plurality of streams can be fed, each containing one or more components for the feed mixture. For example, one feed stream can consist essentially of water.

Preferably the feed comprises sufficient water to substantially suppress formation of lactic acid oligomers and ethyl lactate oligomers in the first liquid effluent and the second fluid effluent. In one embodiment of the invention, the first liquid effluent is substantially liquid. Preferably the vapor product stream from the second vessel comprises at least 5% by weight each of ethyl lactate, ethanol, and water.

The second liquid effluent can optionally be recycled to the first vessel.

The feed can take a variety of forms. For example, the feed can contain lactic acid, lactic acid oligomers, and ethanol. As another example, the feed mixture can comprise one or more of polylactic acid, polylactide, polyhydroxybutyrate, or one or more other polyesters based substantially on pure or mixed alpha or beta hydroxyacids, and can further comprise water. As yet another example, the feed can comprise more than one alcohol or organic acid, and as a result mixed esters are formed. However in this embodiment the boiling points of the alcohols, esters, and water preferably do not have a range of more than 110° C. from the lowest to the highest boiling point.

The present invention is quite useful in conjunction with fermentation processes, so the feed can comprise crude or partially purified broth derived from fermentation of sugars that has been treated to form an stream of acidic pH. In that situation the feed mixture will typically also comprise one or more impurities selected from the group consisting of inorganic salts, protein fragments, sugar residues, ketones, and metal ions.

In one specific embodiment, the feed mixture comprises lactic acid that is substantially optically pure, that is, at least 90% optically pure and ideally 99% or greater optically pure.

Instead of using a single first vessel and a single second vessel, the process can employ a plurality of either of both, operated in series. For instance, in one embodiment, the second vessel is divided into several sub-vessels operated in series, each with temperature, pressure, catalyst, and average residence time such that they operate with vapor and liquid exit streams that are substantially not in reaction equilibrium, and such that the vapor product stream from each sub-vessel is richer in alcohol and water than the vapor product stream of the subsequent sub-vessel.

If the feed comprises polylactic acid, the feed optionally can be pretreated with hot water at temperatures of about 240° C. and pressures of up to 500 psig prior to entering the first vessel.

It will usually be desirable to include in the process the steps of dehydrating and purifying the vapor product stream and separating from that stream ester and alcohol.

The process and equipment of the present invention are efficient for reaction systems where the feed acid or alcohol or both tend to form unwanted dimers, oligomers, and polymers when dehydrated that reduce the yield of the desired ester product. A two-stage process and equipment is used to achieve separation of time-scales for reaction equilibrium and for mass transfer equilibrium while maintaining high water levels needed to suppress unwanted oligomer formation. This invention is advantageous where the ester product is more volatile than the feed organic acid.

A suitable recycle reactor system can include two vessels, or groups of vessels. The first vessel is operated to give a product that is substantially close to reaction equilibrium. The second vessel involves vapor-liquid equilibration and phase change and produces a liquid reaction effluent that is substantially far from reaction equilibrium. The vapors removed from the second vessel or vessels include water, ester, and alcohol. A recycle stream can be passed from the second vessel group back to the first vessel, device or group.

For successful operation the conditions of temperature, pressure, holdup time, reagent concentration, and catalyst levels in the first vessel or group must be such that reaction equilibrium is approached, while the conditions in the second vessel or group must be such that reaction equilibrium in the liquid effluent is not substantially approached.

For this invention, sufficient water is required as part of the feed to the esterification reaction. If the water content of the alcohol and acid used as feedstocks to the system are too low, then water must be added. This is unusual as esterification reactions are usually driven by the removal of water. In addition to requiring water in the feed, appropriate balancing of rates of alcohol and acid feeds is necessary for best operation.

The process and equipment of the present invention can operate at high levels of water in the reaction system with good energy efficiency and good yield.

This invention is of particular value for esters made by reacting methanol, ethanol, propanol, isopropanol, isobutanol, tert-butanol, 1-butanol, or pentanols with any of the following organic acids:

aliphatic alpha hydroxy monocarboxylic acids containing from 2 to 10 carbon atoms, such as hydroxyacetic acid, lactic acid and alpha hydroxy-butyric acid;

aliphatic beta hydroxy monocarboxylic acids containing from 2 to 10 carbon atoms, such as β-hydroxy propionic acid and 2-hydroxy-butyric acid;

gamma and delta hydroxyacids;

other polyfunctional compounds that include both acid and alcohol groups.

The present invention differs from prior art processes in several ways, such as the ability to use a wider range of alcohols, higher temperatures, less alcohol, and more water. The present invention makes use of the separation of vessels in an esterification system to allow independent control of the temperature, holdup time, recirculation rate, pressure, vapor fraction, catalyst level, and feed ratios. A feed dehydration step is not required in the present invention.

DESCRIPTION OF ILLUSTRATIVE EMBODIMENTS

Figure 1:
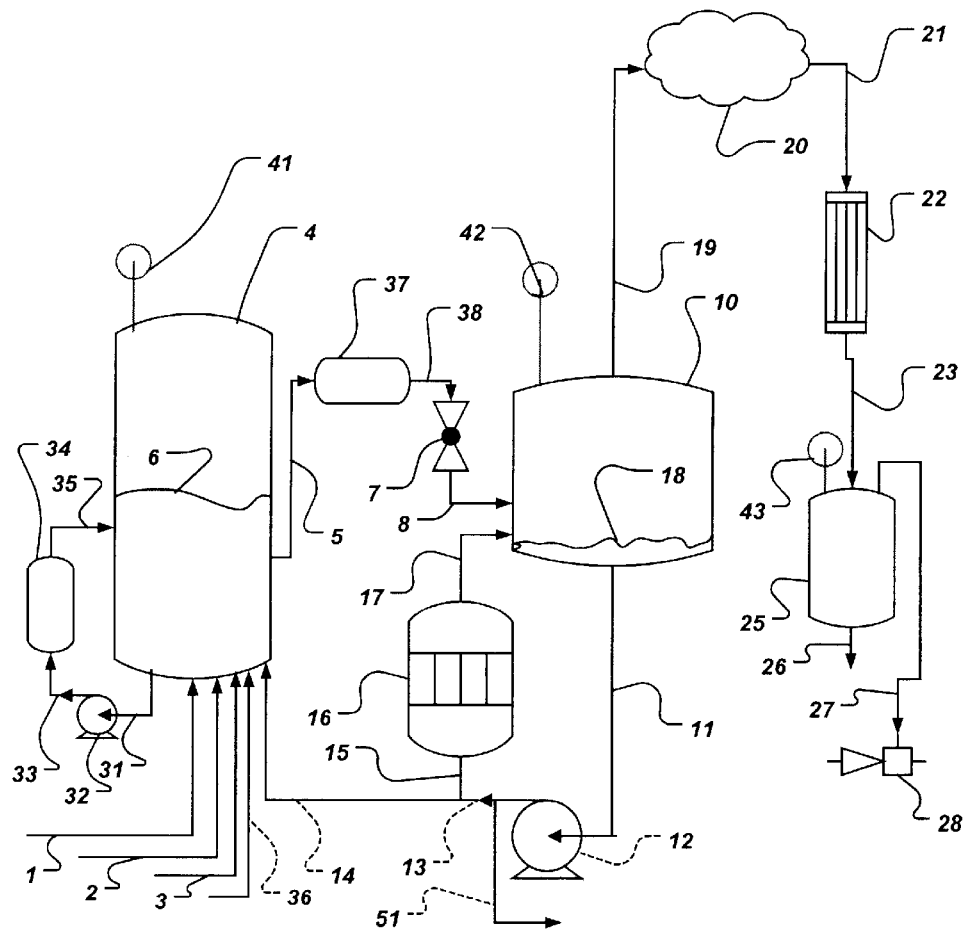
FIG. 1 is a process flow diagram for one embodiment of the present invention.

The following definitions are used in this patents:

Reaction equilibrium: the condition where the chemical species are in reaction equilibrium within a single given phase, such as a liquid phase.

Vapor-liquid equilibrium: the condition where there are at two phases, one vapor and one liquid and there is a physical equilibrium between them.

Lactic acid: the monomeric free lactic acid as is commonly found is dilute aqueous solutions.

"88% lactic acid" and "lactic acid of commerce" refer to a typical commercially available lactic acid, which is actually a mixture of monomeric lactic acid, linear dimer lactic acid or lactoyl lactic acid, short chain lactic acid oligomers, water, and also a small quantity of cyclic dimer lactic acid or lactide. When this lactic acid is diluted in a large excess water, it will slowly hydrolyze or convert to all monomeric form lactic acid.

Ethyl lactoyl-lactate: This species is formed when ethyl lactate reacts with lactic acid via an esterification reaction with the elimination of a single molecule of water. Ethyl lactoyl-lactate has three functional groups comprising two ester groups and one secondary alcohol group. The species ethyl lactoyl-lactate can also be formed by the esterification reaction of lactoyl-lactic acid with ethanol and the elimination of water Ethyl lactate: This ester is formed by the reaction of lactic acid and ethanol.

Lactoyl-lactic acid: This species is formed when two lactic acid molecules react via an esterification reaction with the elimination of a single molecule of water. Lactoyl lactic acid has three functional groups—a secondary alcohol, an ester, and an organic acid.

Lactate oligomers: short chain polyesters based on lactic acid. The smallest molecule referred to here is lactoyl-lactoyl-lactic acid, which is a linear trimer ester of lactic acid. The next in the series is lactoyl lactoyl lactic acid, which is a linear tetramer of lactic acid. Each lactic acid molecule is linked to the next in the chain by an ester linkage. All the lactate oligomers have one terminal free organic acid, one free secondary alcohol group, and two or more ester linkages. Each time an additional lactic acid molecule is added to the polyester chain, one molecule of water is eliminated. Thus, conditions which favor removal of water will drive the formation of these oligomers. Conversely, addition of water will tend to drive the reaction equilibrium back towards monomeric lactic acid.

Ethyl lactate oligomers: These refer to short chain polyesters similar to lactate oligomers, but wherein the free organic acid group has reacted with ethanol to form an additional ester linkage. Thus the ethyl lactate oligomers do not have any free organic acid group. The ethyl lactate oligomers can also be formed by the successive reaction of lactic acid with shorter chain ethyl lactate oligomers or with ethyl lactate.

The key to this invention is the hitherto unconsidered concept that time-scale separation can be used to great advantage in esterification of mixtures that tend to react to form oligomers or polymers upon dehydration. To achieve such time scale separation, the equipment in which the processes of reaction equilibrium and vapor-liquid equilibrium must be physically separated. The reaction equilibrium occurs in one vessel or group of vessels while the vapor-liquid equilibrium occurs in another vessel or group of vessels. The first vessel or group of vessels may involve vapor-liquid equilibrium as well as reaction equilibrium. However, the second vessel or group of vessels will have a liquid effluent that is substantially not in reaction equilibrium. This liquid effluent from the second vessel or set of vessels can be recycled to the first vessel or set of vessels.

The separation of time scales in the two vessels can be achieved in a variety of ways.

In one embodiment of the invention, the first and second vessels are operated at the same pressure, but the residence time in the first vessel is only just sufficient to reach 95% approach to reaction equilibrium and the residence time in the second vessel is no more than one-tenth of that in the first vessel.

In another embodiment of the invention, the separation of time scales is achieved by lowering the pressure in the second vessel such that the temperature of the liquid effluent is low enough that for the holdup time of that liquid stream there is not a substantial approach to equilibrium in the second vessel. This embodiment is usually most favored if the first vessel is operated under substantial pressure, such as 30 to 500 psig, such that the reaction temperature in the first vessel can be kept high and the rate of reaction in the first vessel is high. The second vessel is then operated at pressures for example from 1 to 14 psia. This case leads to some other efficiencies in energy usage.

Yet another embodiment of the invention is to achieve time scale separation by use of different levels of catalyst in the first and second vessels. There must be sufficient catalyst in the first vessel to substantially approach reaction equilibrium. The catalyst that is used in this vessel may be in the form of a heterogeneous catalyst such as an ion exchange resin either located inside the vessel or associated with the first vessel in a recirculation loop. The solid phase catalyst is then removed prior to feeding the reaction liquor to the second reactor. Alternatively, a homogeneous catalyst may be used such as sulfuric acid in the first vessel and then this catalyst can be removed by precipitation or ion exchange prior to feeding to the second vessel.

These approaches are contrary to one common approach used for esterification, so called catalytic distillation, wherein the mass transfer and reaction are combined in a single distillation column.

Yet another embodiment of the invention involves combining two or more of the above approaches of holdup time, temperature or pressure, and catalyst level to achieve the desired separation of time scales.

One embodiment of the present invention is shown in FIG. 1, and includes a first vessel 4 and a second vessel 10 arranged in series.

The reaction may be catalyzed by one or more of a number of methods. A heterogeneous catalyst may be retained in an external recirculation loop comprising draw line 31, pump 32, stream 33, heterogeneous catalyst bed 34 and return line 35. Homogeneous catalyst may be fed to the first vessel 4 via feed line 36 or via recycle line 14. The reaction can also be autocatalysed due to the acidity of one of the reagent feeds, the organic acid feed 1.

Other feed streams include alcohol 2 and optionally water 3. Note that sufficient water may need to be added if the feeds are essentially dehydrated. Also note that for optimal operation, the ratio of organic acid feed 1, alcohol feed 2, water feed 3, and recycle stream 14 need to be adjusted correctly to balance the reaction conditions in the first vessel 4 and the mass transfer conditions in the second vessel 10.

The pressure and temperature in first vessel 4 is preferably monitored with gauges 41 which indicate liquid temperature, vapor pressure, and optionally also vapor temperature. The liquid level 6 in he first vessel 4 is above the point at which liquid effluent reaction product 5 is withdrawn from the vessel.

The reaction product 5 from the first vessel 4 passes to second vessel 10 via the optional catalyst removal unit 37 and optional valve 7. The catalyst removal unit 37 may be a filter or centrifuge or other solid-liquid or solid-vapor separation device for the case of heterogeneous catalysts. For homogeneous catalysis, the catalyst removal device may be an weakly basic anion exchange bed or a cold water washing step or other step to remove the homogeneous catalyst. In the preferred embodiment of the invention, such a device is not used as the time scale separation is achieved by use of the variables of temperature, pressure and holdup time.

The stream 38 passes to pressure letdown valve 7 and pressure reduced stream 8 passes to second vessel 10. Here the liquid level 18 or quantity of liquid present in this vessel is optimally maintained at a low level to minimize holdup time. If reaction in first vessel 4 is primarily in the liquid phase, then heat may be added to the liquid in second vessel 10 by any means well known in the art. By way of example, a recycle loop is shown wherein liquid stream 11 passes to pump 12 and stream 13 is split into stream 14 and stream 15. Stream 15 is heated in heat exchanger 16 and the heated stream 17 returns to second vessel 10. Any other means of adding heat to the liquid in vessel 10 readily known in the art can be used.

The second vessel 10 preferably also includes temperature and pressure measuring devices 42.

If the reaction in the first vessel 4 is primarily in the vapor phase, then the second vessel 10 may involve partial condensation instead of partial evaporation. Heat removal from the liquid stream in vessel 10 can be by any means known in the art. It is not illustrated in FIG. 1.

The vapor removed from second vessel 10 may be one or several different vapor streams. These vapor streams 19 contain the formed ester product, water, and any excess alcohol. The vapors pass to any of a variety of separation process steps 20 such as vapor phase permeation, partial condensation, absorption, adsorption, distillation, extractive distillation, or condensation and pervaporation. The purpose of these various processes 20 is to separate the formed ester product from the alcohol and water streams. One of the streams 21 from any of these processes will pass to some sort of optional condensation system 22, possibly a receiver vessel 25. A product stream 27 is taken from the receiver 25 and eventually to a vacuum or pressure control system 28. This system 28 will be important in that it will control the consequent pressure in vessel 10. Control of the pressure in vessel 10 is important to control the temperature and hence rate of reaction in vessel 10.

The receiver vessel 25 preferably includes temperature and pressure measuring devices 43. A bottom stream can be withdrawn from the receiver 25 also.

As discussed above, the time scale separation requires that the rate of reaction in the second vessel 10 be low enough that the mass transfer occurs without substantial approach to reaction equilibrium of the liquid phase effluent 14 from vessel 10.

Note that in the event of the system being run continuously, one or several of the feed streams may contain salts, sugars, or other non-volatile impurities. As the recycle loop between the vessels 4 and 10 is operated over time, the concentration of these impurities in the system will rise to a point where they need to be removed by some in process method such adsorption, precipitation, filtration, etc., or alternatively as a purge stream 51.

Although shown with a single first vessel 4 and a single second vessel 10, the process can alternatively use a plurality of such vessels. For example, there can be a plurality of first vessels arranged in series, with the liquid effluent from the last in that series feeding to the first in a series of second vessels, also arranged in series. Other arrangements using multiple vessels are also possible. The vessels can for example be one continuous stirred tank reactors (CSTR), pipeline or plug flow reactors (PFR), or any other common vessel or group of vessels suitable for undertaking liquid or vapor phase reactions.

The present invention can be further understood from the following examples.

EXAMPLE 1

Vapor-Liquid Equilibrium in Vessel 2

A glass vessel was charged with a mixture of lactic acid, water, ethyl-lactate, and ethanol as shown in Table 1. It was heated to boiling point and stirred. Overhead vapors were drawn off via an overhead vapor line to a condenser. A mixture of ethanol, ethyl lactate, and water as shown in Table 1 was fed continuously over a period of 5 hours and 44 minutes via a subsurface liquid addition line. The vessel heat input rate was adjusted to obtain a constant level in the vessel. The temperature of the liquid in the pot was about 105° C. and the vapor 101–103° C.

Three samples of overhead vapor taken during the run were analyzed and showed similar concentrations. The composition of the second such sample is shown in Table 1. The final pot liquor is shown in Table 1 also.

Note that in this experiment the subsurface feed did not contain lactic acid. This test was to examine vapor-liquid equilibrium conditions and determine if an overhead vapor rich in ethyl lactate could be removed from a slowly reacting or non-reacting broth.

The molar ratio of total ethyl groups to total lactyl groups in the overhead vapor is seen in this case to be about 6:1. The liquor is in reaction equilibrium with a K-value of 2.80, where K is the molar concentration ratio K=[ethyl-lactate]*[water]/([ethanol]*[lactic acid]). Here [ ] means mole/liter. This represents the limit of technology previously reported, wherein a relatively high ratio of ethanol to lactic acid must be used if the vapor-liquid equilibrium and the reaction equilibrium occur in the same vessel. To obtain more efficient usage of ethanol and lower steam and energy costs, a more effective method is necessary for conducting the reaction and vapor-liquid equilibration process.

Note that neither this example and nor Example 2 represent a process that would likely be used commercially. This is because the feed in both examples is a mixture that contains only ethyl lactate, ethanol, and water. This stream is fed to the vessel as part of the study of the vapor-liquid equilibrium conditions. Results from these studies are then used in calculational models of the process combining the reaction equilibrium in vessel 1 and the vapor liquid equilibrium in vessel 2.

TABLE 1

|  | Initial Charge (mmoles) | Continuous feed (mmoles) | Overhead Vapor (mmoles) | Final Liquid from reactor (mmoles) |
|---|---|---|---|---|
| Water | 355 | 1064 | 1341 | 243 |
| Lactic acid | 333 | 0 | trace | 333 |
| Ethyl lactate | 530 | 400 | 291 | 653 |
| Ethanol | 115 | 1377 | 1459 | 170 |
| K-ratio | 4.92 |  |  | 2.80 |

EXAMPLE 2

Vapor-Liquid Equilibrium in Vessel 2

This example differs from the case of Example 1 in that the vessel was run hotter and that the feed mixture was fed at a higher rate. The total elapsed time for the experiment was 3 hours and 2 minutes.

No catalyst was added to this mixture, thereby simulating a process where this reaction mixture is prepared using a heterogeneous catalyst in the reaction vessel.

Analytical results for samples from this reaction are shown in Table 2. The bottoms had a K ratio of 4.74, showing that in a non-reaction equilibrium, liquid can be obtained in the bottoms which is in vapor-liquid equilibrium with the overhead. Average pot temperature was 117° C. and average overhead vapor was 110° C. The ratio of total ethyl groups to total lactyl groups in the overhead vapor was 5.05:1.0 in this case.

Once again, this example shows vapor-liquid equilibrium but does not show an operable process, because the feed mixture, as in Example 1, was a mixture of only ethyl lactate, ethanol, and water and did not contain lactic acid.

TABLE 2

|  | Initial Vessel Liquid Charge | Continuous Liquid Feed | Final Vessel Liquid | Total Overhead Vapor |
|---|---|---|---|---|
| lactic acid | 0.279 | 0.000 | 0.165 | trace |
| lactoyl lactate | 0.117 |  | 0.067 | trace |
| glucose | 0.057 |  | 0.057 | none |
| glycine | 0.133 |  | 0.164 | none |
| ethyl lactate | 0.545 | 0.335 | 0.478 | 0.322 |
| ethyl lactoyl lactate |  |  | 0.081 | trace |
| ethyl lactoyl lactoyl lactate |  |  | 0.023 | trace |
| water | 0.357 | 0.965 | 0.132 | 1.360 |
| ethanol | 0.330 | 1.233 | 0.081 | 1.304 |
| All E | 0.874 | 1.567 | 0.6395 | 1.6267 |
| All L | 1.0566 | 0.3346 | 1.007 | 0.3223 |
| "K-ratio" = EL* W/L/E | 1.490 |  | 4.744 |  |

This example indicates that more favorable ratio of ethyl-groups to lactyl-groups in the overhead vapor can be obtained if the final vessel liquid is not at reaction equilibrium.

EXAMPLE 3

Simulated Process with Recycle and Two Vessels

Vapor-liquid equilibrium data were used to create a simulation model of two vessels connected with recycle. The first vessel was operated in the simulation at sufficient temperature, pressure, holdup time, and catalyst level such that the liquid effluent is substantially at reaction equilibrium. The second vessel was operated at lower levels of one or more of temperature, holdup time, or catalyst level than the first vessel, such that the liquid effluent from vessel 2 did not approach reaction equilibrium.

A feed of 68,229 lb/hr of a wet ethanol stream containing 90% ethanol and 10% water was fed to vessel 1, together with 28,120 lb/hr of a solution that was nominally 80% lactic acid and 20% water. Either or both streams may contain substantial impurities, although they are not modeled with such in this example. Additionally to vessel 1 was fed a recycle stream from vessel 2. This stream may be at any of a range of floarates as shown in the next example. For this example, the flowrate was selected to be 59,500 lb/hr. The three feed streams were combined. The molar reaction K-ratio for the combined feed stream was 1.96. This was less than the equilibrium value of 2.85 and thus reaction could proceed for the formation of ethyl lactate in the first vessel.

Vessel 1 acted as a plug flow reactor and reached reaction equilibrium. The ethanol, ethyl lactate, lactic acid, and water were in reaction equilibrium. The equilibrium constant depends on the level of ethanol, the temperature, and the level of water. Under these conditions, for purposes of illustration, a value of 2.85 for the molar reaction equilibrium constant was chosen. The liquid effluent from vessel 1 comprised. approximately, the following: ethanol 52,908 lb/hr; water 18,446 lb/hr; ethyl-lactate 69,494 lb/hr, and lactic acid 15,000 lb/hr. This illustrative example does not consider dimers or oligomers of lactic acid or of ethyl lactate. However, in later examples we shall see that this does not materially affect the general nature of the result.

This example used calculated estimations of the vapor-liquid equilibrium. The effluent from vessel 1 was fed to vessel 2. Sufficient heat and/or vacuum is applied to vessel 2 to remove an overhead vapor of the following composition: ethanol 49,900 lb/hr; water 16,900 lb/hr; ethyl lactate 29,500 lb/hr, and a small quantity of lactic acid. The liquid residue in vessel 2 comprised the balance of the material: ethanol 3,000 lb/hr; water 1,500 lb/hr; ethyl lactate 40,000 lb/hr, and lactic acid 15,000 lb/hr. This liquid residue formed the 59,500 lb/hr that is recycled to the first vessel. The molar reaction K-ratio for this stream was 59.37. This was far above the equilibrium value of 2.85 and shows that vessel 2 was not near reaction equilibrium.

The vapor liquid equilibrium process occurring in vessel 2 was modeled approximately here, and thus this example was a close but not exact representation of real behaviour. The molar vapor-liquid equilibrium K-values in the model were as follows: ethyl-lactate 0.5, water 1.0, and ethanol 3.8. Under similar conditions in Example 1 above, real experimental K-values were observed of ethyl-lactate 0.49, water 1.05, and ethanol 3.80.

EXAMPLE 4

Varying the Recycle Ratio

An example similar to Example 3 was modeled with the recycle rate being varied. The ethanol feed was 15 ton/hour of 90% ethanol 10% water. The lactic acid feed was 5.6 ton/hour of 80% nominal lactic acid with 20% nominal water, on a weight basis. The recycle stream from vessel 2 to vessel 1 was varied from 5 ton/hour to as much as 1,000 ton/hour.

It is found that with a recycle rate of less than 11 tons/hour, there was insufficient lactic acid in vessel 1 for forward reaction to occur. Thus if the recycle is insufficient, then the reaction cannot proceed. At a recycle rate of 10 ton/hour, the reaction equilibrium constant in vessel 1 would need to be 3.091 for reaction to proceed at all. This is higher than the true value of 2.56 to 2.85 for this system. As the recycle rate was increased to 80 ton/hour, the reaction K-ratio of the reagents feeding vessel 1 dropped to 2.061. At this ratio, the average rate of reaction in vessel 1 will be greatest.

It was found that with recycle rates above 80 tons/hour the K-ratio started to increase again. Thus in terms of average reaction rate, the recycle rate of 80 tons/hour represented an optimum. Note however that increasing the recycle ratio tends to increases the mass flowrate through the reactor. The optimum reactor size is determined by a combination of the effect of recycle ratio on rate and the effect of recycle ratio on mass rate. The optimum for this set of conditions will be between 20 and 50 tons/hour. This represents a recycle rate equal to 0.97 to 2.43 pounds per hour of recycle for each pound per hour of total feed streams.

EXAMPLE 5

A mixture of lactic acid, ethyl lactate, ethanol, and water was prepared by refluxing a mixture of ethyl-lactate, lactic acid, water and ethanol overnight (for 12 hours) with 0.1% w/w sulfuric acid at atmospheric pressure. A sample of this mixture was analysed as containing the following: ethanol 19.53% w/w; water 9.68% w/w; free lactic acid monomer 16.4% w/w; and ethyl lactate 48.95% w/w. A small vapor sample collected during equilibration above this sample contained the following: ethanol 80.41% w/w; water 19.56% w/w; free lactic acid monomer 0.018% w/w; and ethyl lactate 5.34% w/w. This shows that vapor over a boiling reaction equilibrium mixture under these conditions contains relatively low levels of ethyl lactate. This refluxing represents the reaction vessel 1.

The liquid mixture was fed at 10 gram/minute to a wiped film evaporator operating at 260 mm Hg absolute pressure. The heating element was adjusted to obtain a 1:1.98 mass ratio of overheads condensate collected to liquid bottoms liquor. This represents a recycle rate equal to 1.98 pounds per hour of recycle for each pound per hour of total feed streams. The wiped film evaporator in this case is vessel 2. Note that the liquid effluent was not in reaction equilibrium for ethyl-lactate formation. Also note that two other constants calculated for the formation of lactic acid dimers and for the formation of the ethyl-lactyl-lactate oligomer have increased dramatically in the bottoms from the wiped film evaporator. These show that system was not in reaction equilibrium as it exits this vessel 2. Note that the catalyst was not removed from the liquid. A wiper speed of 120 rpm was used in the wiped film still equipment.

TABLE 3

| | Continuous feed wt % | Overhead Vapor wt % | Final Liquid from reactor wt % |
| --- | --- | --- | --- |
| Water | 19.53 | 23.98 | 1.48 |
| Lactic acid | 16.4 | 0.16 | 24.9 |
| Ethyl lactate | 48.95 | 29.46 | 71.08 |
| Ethanol | 19.53 | 51.20 | 2.80 |
| Molar K-ratio for formation of ethyl-lactate | 2.88 | | 3.05 |
| Molar K-ratio for formation of lactoyl-lactate | 0.58 | | 9.12 |
| Molar K-ratio for formation of ethyl-lactoyl-lactate | 1.33 | | 20.80 |

EXAMPLE 6

An experiment similar to that of the previous example was undertaken, but the bottoms were successively recycled four times, identified here as Runs 1, 2, 3, and 4, from vessel 2, the vapor-liquid separation device or wiped film evaporator, to vessel 1, the reaction equilibrium vessel. Upon each recycle, fresh ethanol and 88% lactic acid was added to the bottoms prior to heating and reacting in vessel 1. Catalyst was added for the first cycle but not for subsequent cycles. The total mass of material processed in the vessel 1 reactor in each cycle was, for runs 1 through 4 respectively, 3386 grams, 3083 grams, 2987 grams, and 2830 grams. This material was then fed to vessel 2. The quantity of overhead vapor collected in each case was 1524, 1445, 1357, and 1349 grams. This represented in total about 20 hours of operation for the four recycle tests. Once again we can calculate the K value for the liquid from the final vessel 2 sample and will find that it is far from reaction equilibrium. The overhead vapors in each case are rich in ethyl-lactate, the desired product.

TABLE 4

| | Liquid product from vessel 1 wt % | Overhead Vapor 1 wt % | Overhead Vapor 2 wt % | Overhead Vapor 3 wt % | Overhead Vapor 4 wt % | Final Liquid from vessel 2 wt % |
|---|---|---|---|---|---|---|
| Water | 9.81 | 20.89 | 16.39 | 16.83 | 16.65 | 0.92 |
| Lactic acid | 16.40 | 0.33 | 0.35 | 0.33 | 0.36 | 22.90 |
| Ethyl lactate | 52.19 | 41.19 | 46.70 | 46.76 | 46.63 | 62.96 |
| Ethanol | 18.99 | 44.14 | 39.47 | 37.94 | 37.90 | 1.04 |
| Molar K-ratio for formation of ethyl-lactate | 3.204, which is at reaction equilibrium for these conditions | | | | | 4.74 |

The preceding description of specific embodiments of the present invention is not intended to be a complete list of every possible embodiment of the invention. Persons skilled in this field will recognize that modifications can be made to the specific embodiments described here that would be within the scope of the present invention.

What is claimed is:

1. A process for producing an ester, comprising the steps of:
   a. feeding to a first vessel a feed that comprises organic acid, alcohol, and water, whereby organic acid and alcohol react to form monomeric ester and water, wherein the monomeric ester has a lower boiling point than the organic acid, and the feed is not dehydrated, and whereby a first liquid effluent is produced that comprises as its components at least some ester, alcohol, and water, the components of the first liquid effluent being substantially in reaction equilibrium; and
   b. feeding the first liquid effluent to a second vessel, whereby a vapor product stream and a second liquid effluent stream are produced, the vapor stream comprising ester, alcohol, and water, wherein the second vessel is maintained at vapor-liquid equilibrium but not at reaction equilibrium; wherein at least one of temperature, pressure, and residence time is greater in the first vessel than in the second vessel.

2. The process of claim 1, where the first vessel is operated at a pressure $P_1$ and the second vessel is operated at a pressure $P_2$, where $P_1$ and $P_2$ are the same, and the average residence time of the feed in the first vessel is at least 10 times longer than the average residence time of the first liquid effluent in the second vessel.

3. The process of claim 1, where the first vessel is operated at a temperature $T_1$ and the second vessel is operated at a second temperature $T_2$ that is sufficiently lower than $T_1$ so that the contents of the second vessel are not at reaction equilibrium.

4. The process of claim 3, where the first vessel is operated at a pressure $P_1$ that is from about 30–500 psig and the second vessel is operated at a pressure $P_2$ that is from about 1–14 psia.

5. The process of claim 1, where catalyst is added to the first vessel in an amount sufficient to catalyze the formation of the ester, and where at least some of the catalyst is removed from the first liquid effluent before it enters the second vessel, so that the contents of the second vessel are not substantially close to reaction equilibrium.

6. The process of claim 5 wherein the catalyst is heterogeneous in the first vessel and is not present in the second vessel.

7. The process of claim 5 wherein the catalyst is homogeneous in the first vessel and is removed from the first liquid effluent via washing prior to the first liquid effluent entering the second vessel.

8. The process of claim 1 wherein both the temperature and pressure in the first vessel are greater than that in the second vessel.

9. The process of claim 1 wherein the second vessel is operated under pressure greater than atmospheric but with short residence time.

10. The process of claim 1 wherein the first vessel is operated under pressure greater than atmospheric pressure.

11. The process of claim 1 wherein the first vessel is operated in a liquid phase with pressures that suppress vaporization and with temperatures up to 220° C. without any added catalyst.

12. The process of claim 1 wherein the first vessel is operated at a liquid temperature of from 150 to 220° C. and the second vessel is operated with an exit vapor temperature of from 30 to 100° C.

13. The process of claim 1, where the organic acid is selected from the group consisting of mono-, di-, and tricarboxylic acids having 3–8 carbon atoms.

14. The process of claim 1, where the organic acid is selected from the group consisting of:
   acetic acid, succinic acid, citric acid, malic acid, lactic acid, hydroxyacetic acid, pyruvic acid, itaconic acid, formic acid, oxalic acid, propionic acid, beta-hydroxybutyric acid, and mixtures thereof.

15. The process of claim 1, where the alcohol is an aliphatic alcohol having from 1–20 carbon atoms.

16. The process of claim 8, where the aliphatic alcohol has from 1–12 carbon atoms.

17. The process of claim 1, where the alcohol is selected from the group consisting of i-butanol, t-butanol, n-butanol, i-propanol, n-propanol, ethanol, and methanol.

18. The process of claim 1 where more than one feed stream is fed to the first vessel, and one of the feed streams consists essentially of water.

19. The process of claim 1, where the organic acid is lactic acid.

20. The process of claim 19 wherein the vapor product stream from the second vessel comprises at least 5% by weight each of ethyl lactate, ethanol, and water.

21. The process of claim 20 wherein the first liquid effluent and the second fluid effluent comprise no lactic acid oligomers or ethyl lactate oligomers.

22. The process of claim 1 wherein at least part of the second liquid effluent is recycled to the first vessel.

23. The process of claim 1 wherein the feed contains lactic acid, lactic acid oligomers, and ethanol.

24. The process of claim 1 wherein the feed comprises crude or partially purified broth derived from fermentation of sugars that has been treated to form an stream of acidic pH.

25. The process of claim 1 wherein the feed comprises one or more impurities selected from the group consisting of inorganic salts, protein fragments, sugar residues, ketones, and metal ions.

26. The process of claim 1 wherein the feed comprises lactic acid that is at least 90% optically pure.

27. The process of claim 1 wherein the second vessel is divided into several sub-vessels operated in series, each with temperature, pressure, catalyst, and average residence time such that they operate with vapor and liquid exit streams that are not in reaction equilibrium, and such that the vapor product stream from each sub-vessel is richer in alcohol and water than the vapor product stream of the subsequent sub-vessel.

28. The process of claim 1 wherein the feed comprises one or more of polylactic acid, polylactide, polyhydroxybutyrate, and wherein the feed further comprises water.

29. The process of claim 1 wherein the feed comprises one or more polyesters based on pure or mixed alpha or beta hydroxyacids, and wherein the feed further comprises water.

30. The process of claim 1 wherein feed comprises polylactic acid and is pretreated with hot water at temperatures of about 240° C. and pressures of up to 500 psig prior to entering the first vessel.

31. The process of claim 1, further comprising the steps of dehydrating and purifying the vapor product stream and separating from that stream ester and alcohol.

32. The process of claim 1 wherein the feed comprises more than one alcohol or organic acid, and mixed esters are formed, provided that the boiling points of the alcohols, esters, and water do not have a range of more than 110° C. from the lowest to the highest boiling point.

33. A process for producing a lactic acid ester, comprising the steps of:

a. feeding to a first vessel a feed that comprises lactic acid, at least one aliphatic alcohol having from 1–20 carbon atoms, and water, whereby lactic acid and the alcohol react to form a monomeric lactic acid ester and water, wherein the lactic acid ester has a lower boiling point than lactic acid, and the feed is not dehydrated, and whereby a first liquid effluent is produced that comprises as its components at least some lactic acid ester, aliphatic alcohol, and water, the components of the first liquid effluent being substantially in reaction equilibrium; and b. feeding the first liquid effluent to a second vessel, whereby a vapor product streamand a second liquid effluent stream are produced, the vapor stream comprising lactic acid ester, aliphatic alcohol, and water, wherein the second vessel is maintained at vapor-liquid equilibrium but not at reaction equilibrium; and wherein at least one of temperature, pressure, and residence time is greater in the first vessel than in the second vessel.

* * * * *

UNITED STATES PATENT AND TRADEMARK OFFICE
CERTIFICATE OF CORRECTION

PATENT NO. : 6,664,413 B1
DATED : December 16, 2003
INVENTOR(S) : Michael Charles Milner Cockren It is certified that error appears in the above-identified patent and that said Letters Patent is hereby corrected as shown below:

Column 18,
Line 13, delete "streamand" and insert -- stream and --.

Signed and Sealed this

Twenty-fourth Day of February, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,664,413 B1
APPLICATION NO. : 09/196266
DATED : December 16, 2003
INVENTOR(S) : Michael Charles Milner Cockrem It is certified that error appears in the above-identified patent and that said Letters Patent is hereby corrected as shown below:

In column 16, claim 16, line 32, delete "claim 8" and insert -- claim 15 --.

Signed and Sealed this

Eleventh Day of September, 2007

JON W. DUDAS
*Director of the United States Patent and Trademark Office*